United States Patent [19]

Beitzke

[11] Patent Number: 4,618,698

[45] Date of Patent: Oct. 21, 1986

[54] PROCESS FOR THE PREPARATION OF A MIXTURE OF AN OPTIONALLY SUBSTITUTED CINNAMIC ACID ESTER AND AN OPTIONALLY SUBSTITUTED β-ALKOXY-β-PHENYL-PROPIONIC ACID ESTER, AND A PROCESS FOR THE PREPARATION OF OPTIONALLY SUBSTITUTED CINNAMIC ACID

[75] Inventor: Bernhard Beitzke, Bergisch Gladbach, Fed. Rep. of Germany

[73] Assignee: Bayer Aktiengesellschaft, Leverkusen, Fed. Rep. of Germany

[21] Appl. No.: 743,533

[22] Filed: Jun. 11, 1985

[30] Foreign Application Priority Data

Jun. 16, 1984 [DE] Fed. Rep. of Germany ....... 3422412

[51] Int. Cl.$^4$ ............................................. C07C 69/76
[52] U.S. Cl. ..................................... 560/060; 560/104
[58] Field of Search .................................. 560/60, 104

[56] References Cited

PUBLICATIONS

Houben–Weyl: "Methoden der Organischen Chemie", Band 8, 1952, Seiten 563–566, Georg Thieme Verlag, Stuttgart, Fed. Rep. of Germany: Sauerstoffverbindungen III.

*Primary Examiner*—Paul J. Killos
*Attorney, Agent, or Firm*—Sprung Horn Kramer & Woods

[57] ABSTRACT

A mixture of an optionally substituted cinnamic acid ester and an optionally substituted β-alkoxy-β-phenyl-propionic acid ester is prepared by reacting an optionally substituted benzaldehyde with an optionally substituted acetic acid ester and an alcoholate in the presence of an alcohol. The reaction can be carried out in a wide temperature range of from −20° C. to +150° C. The ester mixture can be hydrolyzed under acid or alkaline conditions to give optionally substituted cinnamic acid.

11 Claims, No Drawings

PROCESS FOR THE PREPARATION OF A MIXTURE OF AN OPTIONALLY SUBSTITUTED CINNAMIC ACID ESTER AND AN OPTIONALLY SUBSTITUTED β-ALKOXY-β-PHENYL-PROPIONIC ACID ESTER, AND A PROCESS FOR THE PREPARATION OF OPTIONALLY SUBSTITUTED CINNAMIC ACID

The present invention relates to a process for the preparation of a mixture of an optionally substituted cinnamic acid ester and an optionally substituted β-alkoxy-β-phenyl-propionic acid ester by reacting an optionally substituted benzaldehyde with an optionally substituted acetic acid ester and with an alcoholate in the presence of an alcohol. The ester mixture can be hydrolysed under acid of alkaline conditions to give optionally substituted cinnamic acid. The invention therefore also relates to a process for the preparation of optionally substituted cinnamic acid, in which the ester mixture mentioned is first prepared and is then hydrolysed.

The condensation of aromatic aldehydes with acetic acid esters (Claisen-Schmidt reaction) is known in principle (Ber. 23, 976 (1890)). This reaction is carried out in the presence of metallic sodium in order to achieve useful yields of cinnamic acid esters. The presence of alcohols, for example of ethanol, gives unsatisfactory results, as reported in the literature mentioned: besides a low yield of cinnamic acid ester, Cannizzaro reaction of the benzaldehyde to give benzoic acid ester and benzyl alcohol is chiefly thereby observed. This reaction also evidently cannot be completely avoided when alcohol-free sodium methylate is used.

The condensation of benzaldehyde with ethyl acetate is found in revised form in Org. Synth., Coll. volume 1, page 252, John Wiley and Sons, New York 2nd edition 1956. In this case also, the condensation is carried out in the presence of metallic sodium, which, in an inconvenient manner, is melted under xylene, whipped with a stirrer and obtained in the form of fine particles by cooling. The xylene is then decanted and ethyl acetate is added. This revised procedure suggests the addition of very small amounts of alcohol which can convert only about 4 to 5.5% of the sodium into the alcoholate. Larger amounts of alcohol are regarded as harmful in respect of the yield.

However, the use of metallic sodium is industrially expensive and requires particular safety measures, for which reason industrial application is not possible. European Pat. No. 44,976 describes the preparation of methyl p-hexoxy-cinnamate, in which sodium methylate is used as the condensing agent. In this case also, the presence of an alcohol during the condensation reaction is avoided. In order to ensure this, toluene is added to the sodium methylate initially used as a methanolic solution, and the methanol is then distilled off azeotropically as a mixture with toluene.

It has now been found that a mixture of the above-mentioned esters can be prepared in the presence of alcohol, high yields being achieved, even though it was known from the literature that the presence of alcohols produces completely unsatisfactory yields in the preparation of cinnamic acid esters.

A process has been found for the preparation of a mixture of an optionally substituted cinnamic acid ester and an optionally substituted β-alkoxy-β-phenyl-propionic acid ester, which is characterized in that an optionally substituted benzaldehyde is reacted with an excess of an optionally substituted acetic acid ester and with an alcoholate in the presence of an alcohol.

Although the sodium methylate can be introduced into the process in the form of a methanolic solution in the process of European Pat. No. 44,976, it is a great disadvantage that, to remove the methanol, an azeotropic mixture of methanol and toluene is obtained, causing unavoidable working up costs.

It will be assumed that the chemical reactions which proceed in the process according to the invention can be represented by the following equations, the example of the condensation of benzaldehyde with methyl acetate and sodium methylate being shown:

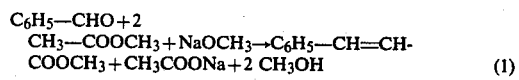

(1)

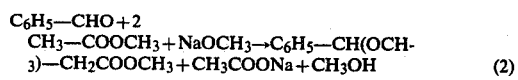

(2)

This condensation reaction using alcoholic alcoholate solutions renders the process easily industrially feasible. Besides the optionally substituted cinnamic acid ester, an optionally substituted β-alkoxy-β-phenylproionic acid ester is formed.

Apart from unsubtituted benzaldehyde, possible optionally substituted benzaldehydes which can be used according to the invention are those which are mono- or poly-substituted, preferably disubstituted and particularly preferably monosubstituted, for example those of the formula

(I)

in which $R^1$ and $R^2$ independently of one another represent hydrogen, alkyl, cycloalkyl, aryl, aralkyl, dialkylamin, diarylamino, halogen, alkoxy, aryloxy, cycloalkoxy, aralkoxy, alkoxycarbonyl, aryloxycarbonyl, alkylcarbonyloxy, alkylthio, arylthio, cycloalkylthio or aralkylthio.

Examples of alkyl radicals, including $R^1$, $R^2$, $R^3$, $R^4$, $R^5$, $R^6$, $R^{11}$ and $R^{12}$, including those in the oxygen-containing or sulphur-containing substituents, are those with 1–16, preferably 1–10 and particularly preferably 1–4, C atoms, such as methyl, ethyl, propyl, butyl, hexyl, decyl, dodecyl and hexadecyl.

Cycloalkyl radicals, including $R^1$, $R^2$, $R^{11}$, $R^{12}$, $R^5$ and $R^6$, including those in the oxygen-containing or sulphur-containing substituents, are those with 4–8, preferably 5 or 6, C atoms arranged in the ring, it being possible for these C atoms optionally to carry one or two methyl or ethyl groups, such as cyclobutyl, cyclopentyl, cyclohexyl, cycloheptyl, cyclooctyl, methylcyclopentyl or methyl-cyclohexyl.

Aryl radicals, including those in the oxygen-containing or sulphur-containing substituents, are to be understood as phenyl, naphthyl, anthryl or diphenyl, preferably phenyl.

Aralkyl radicals, including $R^1$, $R^2$ and $R^5$, inclusing those in the oxygen-containing or sulphur-containing substitutents, are to be understood as those from a phenyl or naphthyl nucleus and a short $C_1$–$C_4$-alkyl chain, such as benzyl, phenylethyl or naphthyl-methyl, preferably benzyl.

The dialkylamino and diarylamino substituents carry alkyl or aryl groups of the abovementioned type.

Examples of halogens which may be mentioned are fluorine, chlorine and bromine, preferably fluorine and chlorine.

Preferably, benzaldehydes of the formula

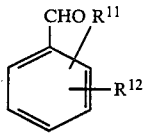

(II)

in which $R^{11}$ and $R^{12}$ independently of one another denote hydrogen, alkyl, cycloalkyl, phenyl, benzyl, dialkylamino, alkoxy, phenoxy or benzyloxy, are employed.

Particularly preferably, benzaldehydes of the formula

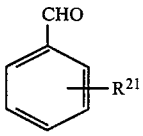

(III)

in which $R^{21}$ represents hydrogen, methyl, ethyl, dimethylamino, methoxy, ethoxy or phenoxy, are employed.

Examples which may be mentioned of optionally substituted acetic acid esters for the process according to the invention are those of the formula $$R^3CH_2\text{—}COOR^4 \qquad (IV)$$

in which
  $R^3$ represents hydrogen or alkyl and
  $R^4$ represents alkyl, phenyl or benzyl.

Alkyl which may be mentioned in the context of the above disclosure is straight-chain or branched alkyl. The phenyl or benzyl substitutents mentioned can be substituted by methyl, ethyl, methoxy, ethoxy or dimethylamino.

Preferably, methyl acetate, ethyl acetate, butyl acetate or iso-butyl acetate is employed.

Examples which may be mentioned of alcoholates for the process according to the invention are those of the formula $$R^5OMe \qquad (V)$$

in which
  $R^5$ denotes straight-chain or branched alkyl, cycloalkyl or aralkyl and
  Me represents an alkali metal cation or one cation equivalent of the metals magnesium, aluminum or titanium.

The meaning of alkyl, cycloalkyl and aralkyl in formula (V) is the same as that disclosed above. The alkyl radicals $R^5$ can furthermore contain alkoxy groups or polyether groups, since either-alcohols are also suitable alcoholates which can be used according to the invention.

Examples which may be mentioned of alkali metals are lithium, sodium, potassium, rubidium and cesium, preferably lithium, sodium and potassium and particularly preferably sodium.

Preferably, straight-chain or branched $C_1$–$C_4$-alkylalcoholates of sodium or potassium are used; sodium methylate and sodium ethylates may be mentioned in particular.

Examples of alcohols for the process according to the invention are those of the formula $$R^6OH \qquad (VI)$$

in which $R^6$ denotes alkyl, cycloalkyl or benzyl.

The scope of meaning of alkyl and cycloalkyl is that disclosed above. Preferably, methanol, ethanol, butanol and iso-butanol are employed.

The radicals $R^4$, $R^5$ and $R^6$ are in principle independent of one another. However, it is advantageous, especially if transesterifacation reactions are to be avoided, for the radicals $R^4$, $R^5$ and $R^6$ to have the same meaning for carrying out the process.

A solution or suspension of the alcoholate in one of the abovementioned alcohols, preferably in the alcohol from which the alcoholate is derived, for example sodium methylate in methanol, sodium ethylate in ethanol, potassium tert.-butylate in tert.-butanol or sodium iso-butylate in iso-butanol, is used for the process according to the invention. The use of such alcoholate solutions means that the process can easily be carried out industrially, since such alcoholate solutions are readily accessible and can easily be handled, and are also prepared industrially. The alcoholates are in general used in the form of a 5–50% strength by weight, preferably 20–40% strength by weight and particularly preferably 25–35% strength by weight, solution in the alcohol on which they are based. Commercially available technical grade alcoholate solutions are in general 30% strength, for example 30% strength sodium methylate in methanol. Alkali metal alcoholate solutions of the higher alcohols can be prepared by transalcoholisation (Houben-Weyl, 4th edition, volume VI/2, page 13 (1963)) or, particularly advantageously, be dehydration of sodium hydroxide and the corresponding alcohol (European Pat. No. 91,425).

The alcoholate is used in an amount of 1–2 moles per mole of the optionally substituted benzaldehyde, preferably in an amount of 1–1.2 moles. The alcohol is used in an amount of 2–25 moles per mole of alcoholate, preferably 3–15 moles. The optionally substituted acetic acid ester is always kept in the reaction mixture in a molar excess over the optionally substituted benzaldehyde, which is preferably at least 2 moles of acetic acid ester per mole of benzaldehyde, for example the acetic acid ester is employed in an amount of 2–20 moles per mole of the optionally substituted benzaldehyde, preferably in an amount of 3–15 moles and particularly preferably 6–14 moles. When the reaction has ended, the excess acetic acid ester can be recovered by distillation, together with the alcohol, and used for a new batch.

The reaction is carried out at a temperature of $-20°$ C. to $+150°$ C., preferably at $0°$–$100°$ C. and particularly preferably at $20°$–$80°$ C. The process according to the invention can be carried out under normal pressure and/or under increased pressure. The reaction is advantageously carried out under an inert gas, for example under nitrogen, in order to exclude water (atmospheric moisture), carbon dioxide and oxygen.

The reaction in the process according to the invention can be carried out in various ways. Thus, it is possible to introduce the alcoholate solution into a stirred vessel and to meter in a mixture of the optionally substituted benzaldahyde and the optionally substituted acetic acid ester. However, it is also possible to take the alcoholate solution and the optionally substituted acetic acid ester and to meter in the benzaldehyde by itself. It is furthermore possible to take the optionally substituted acetic acid ester and to meter in the benzaldehyde and the alcoholate solution simultaneously but separately. Good results are furthermore obtained if the optionally substituted benzaldehyde and the optionally substituted acetic acid ester are taken and the alcoholate solution is metered in. If the optionally substituted acetic acid ester is metered in, this can additionally also contain alcohol, which is recycled, together with the optionally substituted acetic acid ester, from an earlier batch. In the case where the alcoholate is initially introduced in one of the variants mentioned, this can also be in the form of a suspension and the alcohol can be introduced into the reaction mixture, within the range of the abovementioned amounts, together with one of the reactants to be metered in. In a preferred embodiment, the alcoholate solution is initially introduced and the mixture of the optionally substituted benzaldehyde and the optionally substituted acetic acid ester, optionally together with the alcohol, is metered in. In all the procedure variants mentioned, it is ensured that the optionally substituted acetic acid ester is always present in a molar excess over the optionally substituted benzaldehyde. After all the reactants have been metered in, stirring is continued until the reaction is complete. The end of the reaction can be monitored in a known manner by analytical methods, for example by chromatographic methods.

For working up, in general, water is added to the reaction mixture and the mixture is acidified. Thereafter, the aqueous and organic phases can be separated and the organic phase can be worked up, for example, by distillation in order to obtain the ester mixture of the optionally substituted cinnamic acid ester and the optionally substituted β-phenyl-β-alkoxy-propionic acid ester. Advantageously, however, as much as possible of the excess optionally substituted acetic acid ester is frequently distilled off from the reaction mixture, together with the alcohol, because this distillate can be used in the next reaction batch without further treatment. Only then is water added to the remaining reaction batch, in the manner indicated, and the batch is either worked up by extraction and phase separation, or hydrolyzed in a manner described below. The ester mixture in general consists of 80 to 95% of optionally substituted cinnamic acid ester and 5 to 20% of optionally substituted β-phenyl-β-alkoxy-propionic acid ester.

The joint preparation of an optionally substituted cinnamic acid ester and an optionally substituted β-alkoxy-β-phenyl-propionic acid ester is new. The preparation of a β-alkoxy-β-phenyl-propionic acid ester under the conditions of the condensation reaction described has not hitherto been considered possible.

The ester mixture is used in the perfume and essence industry, in particular because of its content of optionally substituted cinnamic acid ester (Ullmans Encyclopä die der technischen Chemie (Ullmann's Encyclopaedia of industrial chemistry), 4th edition, volume 24, page 592 (1983)). If desired, it is of course also possible for the ester mixture to be separated into its constituents, that is to say the optionally substituted cinnamic acid ester and the optionally substituted β-alkoxy-β-phenyl-propionic acid ester, for example by distillation.

An important method of further processing is, however, hydrolysis of the optionally substituted cinnamic acid ester to give the optionally substituted cinnamic acid. Elimination of the β-alkoxy group from the optionally substituted β-alkoxy-β-phenyl-propionic acid ester takes place here at the same time. This elimination can be carried out under basic or acidic conditions, preferably with aqueous bases.

The invention thus furthermore relates to a process for the preparation of optionally substituted cinnamic acid, which is characterized in that an optionally substituted benzaldehyde is first reacted with an optionally substituted acetic acid ester and with an alcoholate in the presence of an alcohol in the manner described to give the mixture of the esters which is described, and the ester mixture is then hydrolyzed under acid or alkaline conditions.

The ester mixture is hydrolyzed by customary methods (Houben-Weyl, volume VIII, page 418). The hydrolysis is preferably carried out under alkaline conditions. Examples of bases which can be used are aqueous sodium hydroxide solution or aqueous potassium hydroxide solution, preferably aqueous potassium hydroxide solution. Either the crude ester mixture of the optionally substituted cinnamic acid ester and the optionally substituted β-alkoxy-β-phenyl-propionic acid ester which is obtained after distilling off the excess optionally substituted acetic acid ester and the alcohol, or the ester mixture which has been purified, for example, by distillation can be used for the hydrolysis. The base is used in an amount of 1–5 moles, preferably 1.5–2.5 moles, per mole of the esters present in the ester mixture. The hydrolysis is carried out at a temperature of 20°–150° C., preferably 60°–120° C. and particularly preferably at 90°–110° C. The free cinnamic acid is isolated from the hydrolysis batch, for example, by acidification.

Cinnamic acid and substituted cinnamic acids have diverse uses, for example for the preparation of esters for the perfume and essence industry. Sodium cinnamate is furthermore an anti-corrosion agent (Ullmann, volume 24, page 592 (1983)). Cinnamic acid is furthermore an intermediate for the preparation of phenylalanine (Japanese Pat. No. 81/26197, quoted in Chem. Abstr. 95, 95470b; Japanese Pat. No. 78/96388, quoted in Chem. Abstr. 89 213580p, and Japanese Pat. No. 82/122834, Mitsubishi Petrochem.).

EXAMPLE 1

(a) Preparation of the ester mixture 210 g of a 30% strength by weight solution of sodium methylate in methanol were introduced into a 2 liter flash under nitorgen. A mixture of 111.4 g (1.05 moles) of benzaldehyde and 611 g (8.26 moles) of methyl acetate were added dropwise at 60° C. in the course of 70 minutes and the mixture was stirred at 60° C. for 6 hours. 210 ml of 10% strength acetic acid were then added and the phases were separated. The aqueous phase was extracted twice more with 200 ml of toluene each time and the organic phases were combined, dried over $Na_2SO_4$ and distilled. After distilling off the toluene and methyl acetate, the main fraction (132.8 g) was collected under 22 mbar at an overhead temperature of about 128° C., this fraction having the following composition, according to combined gas chromatigraphy/mass spectroscopy analysis (GC/MS):

| | |
|---|---|
| Toluene | 1.1% |
| Benzaldehyde | 1.8% |
| Methyl cinnamate | 86.1% |
| Cinnamic acid | 0.3% |
| Methyl β-phenyl-β-methoxy-propionate | 10.7% |

The last runnings (10.4 g) had the following composition:

| | |
|---|---|
| Methyl cinnamate | 87.7% |
| Cinnamic acid | 7.6% |
| Methyl β-phenyl-β-methoxypropionate | 4.7% |

The sum of the yields of methyl cinnamate, cinnamic acid and methyl β-phenyl-β-methoxy-propionate were 80 mol %, based on the benzaldehyde employed.

Methyl β-phenyl-β-methoxy-propionate has the following $^1$H-NMR spectrum (250 MHz, CDCl$_3$, TMS internal standard): δ=2.72(mc, 2H, CH$_2$), δ=3.2 (s, 3H, OCH$_3$), δ=3.7 (s, 3H, COOCH$_3$), δ=4.7 (mc, 1H, CH), δ=7.3-7.65 (m, 5H, ArH)ppm.

(b) Hydrolysis

The main fraction and the last runnings were combined and heated under reflux with 1.120 g of 10% strength potassium hhdroxide solution (2 moles) for 6 hours. After acidification with 48% strength sulphuric acid and drying, 122.8 g of cinnamic acid of melting point 133° C. were obtained. This corresponds to a yield of 79% of the theoretical yield.

EXAMPLE 2

210 g of a 30% strength solution of sodium methylate in methanol were introduced into a 2 liter four-necked flask with a stirrer, thermometer, dropping funnel and reflux condenser, under nitrogen. A mixture of 111 g (1.05 moles) of benzaldehyde and 593 g (8 moles) of methyl acetate was added dropwise at 60° C. in the course of 1 hour. The mixture was subsequently stirred for 6 hours at 60° C. 210 ml of 10% strength acetic acid were then added and the phases were separated. The aqueous phase was extracted twice more with 200 ml of toluene each time. The organic phases were combined and washed with 200 ml of water. After drying over Na$_2$SO$_4$ and distilling off excess methyl acetate and toluene, 199.6 g of residue were obtained which, according to GC, had the following composition:

| | |
|---|---|
| Toluene | 18.4% |
| Methyl β-phenyl-β-methoxypropionate | 12.5% |
| Methyl cinnamate | 69.1% |

1,120 g of 10% strength potassium hydroxide solution were added to the residue and the mixture was subjected to incipient distillation. After removal of the toluene, the mixture was heated under reflux for 6 hours. After acidification with 48% strength sulphuric acid, 140 g of cinnamic acid of melting point 133° C. were obtained; yield: 90% of the theoretical yield.

EXAMPLE 3

21 g of a 30% strength solution of sodium methylate in methanol were introduced into a 250 ml flask under nitrogen. A mixture of 11.1 g of benzaldehyde and 100 g (1.35 moles) of methyl acetate was added dropwise at a bottom temperature of 60° C. in the course of 1 hour. A sample of the resulting suspension was taken, dissolved in methanol and analysed by gas chromatography/mass spectrometry. Besides methyl acetate, traces of benzaldehyde and the solvent, the sample contained 4.65% of methyl β-phenyl-β-methoxy-propionate and 23.2% of methyl cinnamate.

EXAMPLE 4

210 g of a 30% strength solution of sodium methylate in methanol were introduced into a 2 liter four-necked flask with a stirrer, thermometer, dropping funnel and reflux condenser, under nitrogen. A mixture of 111.4 g (1.05 moles) of benzaldehyde and 1000 g (13.51 moles) of methyl acetate was added dropwise at 60° C. in the course of 1 hour. The mixture was then stirred at 56° C. for a further 6 hours. The excess methyl acetate was then distilled off, together with the methanol, up to an overhead temperature of 57° C. (765.5 g). 500 ml of water were added and the mixture was distilled again up to an overhead temperature of 91° C., 220.7 g of distillate being obtained.

612 g (2 moles) of 18% strength potassium hydroxide solution were added dropwise at a bottom temperature of 90 to 95° C., after which the mixture was stirred under reflux for 6 hours. After clarification with 2.5 g of active charcoal, the mixture was adjusted to pH 3 with 250 ml of 48% strength sulphuric acid at 70° C. and the cinnamic acid was precipitated. The product was filtered off with suction at 20° C. and rinsed three times with 200 ml of water each time. After drying, 142 g of cinnamic acid of melting point 132°-3° C. were obtained; yield: 91% of the theoretical yield.

EXAMPLE 5

1000 g of methyl acetate were introduced into a 2 liter four-necked flask with a stirrer, thermometer, reflux condenser, Claisen-adapter and 2 dropping funnels, under nitrogen, and were warmed to 55° C. 111.4 g (1.05 moles) of benzaldehyde and 210 g of a 30% strength solution of sodium methylate in methanol were then metered in separately, but simultaneously, from the dropping funnels in the course of 1 hour, after which the resulting suspension was stirred at 55° C. for a further 6 hours. After distilling off 828.7 g of methyl acetate/methanol mixture, 500 ml of water were added and distillation was continued up to an overhead temperature of 92° C. 612 g (2 moles) of 18% strength potassium hydroxide solution were added to the residue and the mixture was heated under reflux for 6 hours. After precipitation and isolation of the cinnamic acid as described in Example 4, 133 g of cinnamic acid of melting point 132°-3° C. were obtained; yield: 85.5% of the theoretical yield.

EXAMPLE 6

The procedure followed was as in Example 4, but 296 (4 moles) of methyl acetate were employed. 125 g of cinnamic acid of melting point 134° C. were obtained; this corresponds to a yield of 80% of the theoretical yield.

EXAMPLE 7

The same amounts as in Example 4 were employed, but the mixture of benzaldehyde and methyl acetate was taken and the sodium methylate solution was metered in at 60° C. in the course of 1 hour. The subsequent procedure was a in Example 4, and 126 g of cinnamic acid of melting point 132°-134° C. were obtained; yield: 81% of the theoretical yield.

EXAMPLE 8

The procedure followed was as in Example 4, but 360 g of a 30% strength sodium methylate solution was taken. 340 ml of 48% strength sulphuric acid were required for precipitation of the cinnamic acid. 141.8 g of cinnamic acid of melting point 134° C. were obtained; yield: 91% of the theoretical yield.

EXAMPLE 9

200 g (1.1 moles) of a 30% strength solution of sodium methylate in methanol were introduced into a 1 liter four-necked flask with a stirrer, dropping funnel, reflux condenser and thermometer, under $N_2$. A mixture of 120.1 g (1 mole) of p-methylbenzaldehyde and 592 g (8 moles) of methyl acetate was added dropwise at a bottom temperature of 57°-60° C. in the course of 1 hour. The resulting suspension was stirred at 58° C. for a further 6 hours. The excess methyl acetate was then distilled off, together with the methanol (509 g).

700 ml of $H_2O$ were added to the residue and the pH was brought to 6 with 100 ml of 10% strength acetic acid. The upper phase of the resulting two-phase mixture slowly crystallized completely. After filtering off the crystals with suction and drying, 147 g of substance of melting point 53°-56° were obtained.

Analysis (GC): 92% of methyl p-methylcinnamate, 3% of p-methylcinnamic acid and 5% of methyl β-methoxy-β(4-methylphenyl)-propionate.

A further 10.8 g of substance of melting point 53°-56° C. were obtained by extraction of the aqueous phase with xylene.

Analysis (GC): 85% of methyl p-methylcinnamate, 10% of p-methylcinnamic acid and 5% of methyl β-methoxy-β(4-methylphenyl)-propionate.

The total yield is 89% of the theoretical yield.

What is claimed is:

1. A process for the preparation of a mixture of an optionally substituted cinnamic acid ester and an optionally substituted β-alkoxy-β-phenyl-propionic acid ester which comprises contacting an optionally substituted benzaldehyde with a molar excess of an optionally substituted acetic acid ester and with an alcoholate in the presence of an alcohol.

2. A process according to claim 1 wherein the alcohol is employed in an amount of 2 to 25 moles of alcohol per mole of the alcoholate.

3. A process according to claim 1 wherein the alcoholate is employed in the amount of 1-2 moles per mole of optionally substituted benzaldehyde.

4. A process according to claim 1 wherein the optionally substituted acetic acid ester is always maintained in the reaction mixture in a molar excess over the optionally substituted benzaldehyde.

5. A process according to claim 4 wherein there are at least 2 moles of optionally substituted acetic acid ester in the mixture per mole of optionally substituted benzaldehyde.

6. A process according to claim 1 wherein the optionally substituted benzaldehyde employed is one of the formula

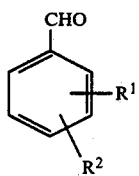

in which $R^1$ and $R^2$ independently of one another represent hydrogen, alkyl, cycloalkyl, aryl, aralkyl, dialkylamino, diarylamino, halogen, alkoxy, aryloxy, cycloalkoxy, aralkoxy, alkoxycarbonyl, aryloxycarbonyl, alkylcarbonyloxy, alkylthio, arylthio, cycloalkylthio or aralkylthio.

7. A process according to claim 1 wherein the optionally substituted acetic acid ester is one of the formula $$R^3CH_2-COOR^4 \qquad (IV)$$

wherein
$R^3$ represents hydrogen or alkyl and
$R^4$ represents alkyl, phenyl or benzyl.

8. A process according to claim 1 wherein the alcoholate is one of the formula $$R^5OMe \qquad (V)$$

wherein
$R^5$ denotes straight-chain or branched alkyl, cycloalkyl or aralkyl and
Me represents an alkali metal cation or one cation equivalent of magnesium, aluminum or titanium.

9. A process according to claim 1 wherein the alcohol is one of the formula $$R^6OH \qquad (VI)$$

in which $R^6$ denotes alkyl, cycloalkyl or benzyl.

10. A process according to claim 1 wherein an optionally substituted benzaldehyde is initially reacted with an optionally substituted acetic acid ester and with an alcoholate in the presence of an alcohol whereby to form a mixture of optionally substituted cinnamic acid ester and optionally substituted β-alkoxy-β-phenyl-propionic acid and thereafter the resultant ester mixture is hydrolyzed under acid or alkaline conditions to yield a cinnamic acid.

11. A process according to claim 6 wherein the optionally substituted acetic acid ester employed is one of the formula $$R^3CH_2-COOR^4 \qquad (IV)$$

wherein
$R^3$ represents hydrogen or alkyl and
$R^4$ represents alkyl, phenyl or benzyl, the alcoholate is one of the formula $$R^5OMe \qquad (V)$$

wherein
$R^5$ denotes straight-chain or branched alkyl cycloalkyl or aralkyl and
Me represents an alkali metal cation or one cation equivalent of magnesium, aluminum or titanium
and the alcohol is one of the formula $$R^6OH \qquad (VI)$$

in which $R^6$ denotes alkyl, cycloalkyl or benzyl, the alcohol is employed in an amount of 2-25 moles per mole of alcoholate, the alcoholate is employed in an amount of 1-2 moles per mole of optionally substituted benzaldehyde and the optionally substituted acetic acid ester is always maintained in the reaction mixture in a molar excess based upon the number of moles of optionally substituted benzaldehyde.

* * * * *

UNITED STATES PATENT AND TRADEMARK OFFICE
CERTIFICATE OF CORRECTION

PATENT NO. : 4,618,698

DATED : October 21, 1986

INVENTOR(S) : Bernhard Beitzke

It is certified that error appears in the above-identified patent and that said Letters Patent are hereby corrected as shown below:

| | |
|---|---|
| Col. 1, line 17 | After "acid" delete "of" and substitute --or-- |
| Col. 2, lines 44, 45 | Delete "dialkylamin" and substitute --dialkylamino-- |
| Col. 3, line 46 | Correct spelling of --substituents-- |
| Col. 3, line 66 | Delete "either" and substitute --ether-- |
| Col. 4, line 7 | Delete "ethylates" and substitute --ethylate-- |
| Col. 4, line 20 | Correct spelling of --transesterification-- |
| Col. 5, line 63 | After "Encyclopä" insert -- " -- |
| Col. 6, line 57 | Correct spelling of --nitrogen-- |
| Col. 7, line 1 | Correct spelling of --chromatography-- |
| Col. 7, line 30 | Correct spelling of --hydroxide-- |

UNITED STATES PATENT AND TRADEMARK OFFICE
CERTIFICATE OF CORRECTION

PATENT NO. : 4,618,698
DATED : October 21, 1986
INVENTOR(S) : Bernhard Beitzke

It is certified that error appears in the above—identified patent and that said Letters Patent are hereby corrected as shown below:

Col. 9, line 2            After "was" delete "a" and substitute --as--

Col. 9, lines 17, 18      Delete "1 liter" and substitute --2 liter--

Signed and Sealed this

Twenty-seventh Day of January, 1987

Attest:

DONALD J. QUIGG

Attesting Officer      Commissioner of Patents and Trademarks